(12) United States Patent
Oeltgen et al.

(10) Patent No.: US 6,380,164 B1
(45) Date of Patent: Apr. 30, 2002

(54) METHOD FOR TREATING CYTOKINE MEDIATED HEPATIC INJURY

(75) Inventors: Peter R. Oeltgen, Winchester; Craig J. McClain; Shirish Barve, both of Lexington, all of KY (US); Paul D. Bishop, Fall City, WA (US)

(73) Assignees: University of Kentucky Research Foundation, Lexington, KY (US); ZymoGenetics, Seattle, WA (US)

( * ) Notice: Subject to any disclaimer, the term of this patent is extended or adjusted under 35 U.S.C. 154(b) by 0 days.

(21) Appl. No.: 09/767,657

(22) Filed: Jan. 23, 2001

Related U.S. Application Data

(63) Continuation of application No. 09/302,821, filed on Apr. 30, 1999.

(51) Int. Cl.[7] .......................... A61K 38/08; C07K 7/06
(52) U.S. Cl. ............................. 514/16; 514/2; 514/893; 514/894; 514/937; 530/300; 530/302
(58) Field of Search .............................. 514/2, 16, 893, 514/894, 937; 530/300, 302

(56) References Cited

PUBLICATIONS

Leist et al., *Activation of the 55 kDa TNF Receptor Is Necessary and Sufficient for TNF–Induced Liver Failure, Hepatocyte Apoptosis, and Nitrite Release*, The Journal of Immunology, 1995, 154: 1307–1316.

Tsutsui et al., *IL–18 Accounts for Both TNF–α–and Fas Ligand–Mediated Hepatotoxic Pathways in Endotoxin–Induced Liver Injury in Mice*, The Journal of Immunology, 1997, 159: 3961–3967.

Bohlinger et al., *Interleukin–1 and Nitric Oxide Protect Against Tumor Necrosis Factor α–Induced Liver Injury Through Distinct Pathways*, Hepatology 1995; 22: 1829–1837.

Leist et al., *Murine Hepatocyte Apoptosis Induced in Vitro and In Vivo by TNF–α Requires Transcriptional Arrest*, The Journal of Immunology, 1994, 153: 1778–1788.

Root et al., *Septicemia and Septic Shock*, Part Five Infectious Diseases, Section 3 Clinical Syndromes, Harrison's Principles of Internal Medicine, 12th Ed., McGraw–Hill, 1991, 502–507.

Hill et al., *Cytokines and Liver Disease*, Cytokines in Health and Disease, Second Edition, Revised and Expanded, 27: 401–425 (1997).

Reisine et al., *Opioid Analgesics and Antagonists*, Goodman and Gilman's The Pharmacological Basis of Therapeutics, 9th Ed., 1995, Section III Drugs Acting on the Central Nervous System, 23: 521–555.

Morgan, Regulation of human B lymphocyte activation by opioid peptide hormones—Inhibition of IgG production by opioid receptor class (gamma–, kappa–, and delta—) selective agonists, Journal of Neuroimmunology, vol. 65, No. 1, 1996, pp. 21–30.

Malaguarnera et al., Elevation of interleukin 6 levels in patients with chronic hepatitis due to hepatitis C virus, Journal of Gastroenterology, vol. 32, 1997, pp. 211–215.

House et al., A comparative study of immunomodulation produced by in vitro exposure to delta opioid receptor agonist peptides, Peptides, (1996) 17 (1) 75–81.

Thornton, Jr. et al., Opioid peptides and primary biliary cirrhosis, BMJ, vol. 297, No. 6662, 1988, pp. 1501–1504.

Thomas et al., Structure–activity relationships of a series of 'D–Ala2! deltorphin I and II analogues; in vitro blood–brain barrier permeability and stability, Journal of Pharmacology and Experiential Therapy, vol. 281, No. 2, 1997, pp. 817–825.

*Primary Examiner*—Christine J. Saoud
*Assistant Examiner*—Fozia Hamud
(74) *Attorney, Agent, or Firm*—Wood, Herron & Evans, LLP

(57) ABSTRACT

A method of modulating cytokine mediated hepatic injury by administering deltorphins to a mammal. Deltorphin I SEQ ID NO:1, deltorphin II SEQ ID NO:2 or combinations of deltorphins I SEQ ID NO:1 and II SEQ ID NO:2 may be administered. A deltorphin concentration in the range of about 0.5 mg/kg to about 20 mg/kg in a physiologically acceptable formulation blocks a cytokine cascade in a murine model of septic shock. A therapeutic method of modulating cytokine mediated acute inflammatory, trauma induced and toxin induced hepatic injury, particularly via tumor necrosis factor modulation, is thus disclosed.

12 Claims, No Drawings

SEQUENCE LISTING

<160> NUMBER OF SEQ ID NOS: 2

<210> SEQ ID NO 1
<211> LENGTH: 7
<212> TYPE: PRT
<213> ORGANISM: Phyllomedusa bicolor

<400> SEQUENCE: 1

Tyr Ala Phe Asp Val Val Gly
 1               5

<210> SEQ ID NO 2
<211> LENGTH: 7

```
-continued

<212> TYPE: PRT
<213> ORGANISM: Phyllomedusa bicolor

<400> SEQUENCE: 2

Tyr Ala Phe Glu Val Val Gly
 1               5
```

METHOD FOR TREATING CYTOKINE MEDIATED HEPATIC INJURY

This application is a continuation of U.S. application Ser. No. 09/302,821, filed Apr. 30, 1999, which claims the benefit of U.S. application Ser. No. 09/071,255, filed May 1, 1998.

FIELD OF THE INVENTION

The invention relates to the use of deltorphins to attenuate or prevent cytokine mediated hepatic injury.

BACKGROUND

Hepatic injury can be caused by a number of different agents including viruses such as Hepatitis A, B, C, D and E, both gram positive and gram negative bacteria, chemical agents such as ethanol, carbon tetrachloride and lead, and by physical trauma resulting in ischemia (ischemic hepatitis) injuries as can occur in right-sided congestive heart failure. It is now believed that all of these types of hepatic injury are caused at least in part by the liver's inflammatory or cytokine response to these agents. The inflammatory response of the liver results in the overexpression of a cascade of inflammatory/acute phase cytokines, such as interleukin-1 (IL-1), tumor necrosis factor (TNF), IL-6, IL-8 and transforming growth factor beta (TGFβ). It is now believed that it is the cascade of these cytokines which is the ultimate cause of much of the hepatic injury resulting from these agents. Thus, there is a need for a therapeutic agent which can be useful in alleviating or modulating the inflammatory response associated with liver disease or injury.

SUMMARY OF THE INVENTION

The present invention fills this need by providing a method of treating or preventing a cytokine mediated hepatic injury in a mammal comprised of administering a pharmaceutically effective amount of a deltorphin to said mammal. The hepatic injury can be an acute inflammatory reaction, as a result of a viral or bacterial infection or a chemical agent such as ethanol, lead, carbon tetrachloride or acetaminophen, or from trauma resulting in ischemia or reperfusion injury in the liver.

The present invention is also directed to a method of treating a viral or bacterial infection-related hepatic damage in a mammal comprised of administering a pharmaceutically effective amount of a deltorphin to said mammal.

The present invention is also directed to a method of treating alcohol induced liver injury in a mammal comprised of administering a pharmaceutically effective amount of a deltorphin to said mammal.

Preferably, the deltorphin is administered in a pharmaceutical composition at a dosage of from about 0.5 mg/kg to about 20 mg/kg, or alternatively lower doses from about 1 µg/kg to about 1000 µg/kg of deltorphin per body weight of the mammal.

Preferably, the mammal is a human.

DETAILED DESCRIPTION

Deltorphins are endogenous linear heptapeptides isolated from skin extracts of the South American frog Phyllomedusa bicolor. These may be further divided into deltorphin I SEQ ID NO:1 and deltorphin II SEQ ID NO:2 depending on their amino acid sequence. Deltorphin I SEQ ID NO:1 has the amino acid sequence Tyr-Ala-Phe-Asp-Val-Val-Gly-NH$_2$ with alanine as either the D- or L-isomer. Deltorphin II SEQ ID NO:2 has the amino acid sequence Tyr-Ala-Phe-Glu-Val-Val-Gly-NH$_2$ with alanine as either the D- or L-isomer. Either deltorphin I SEQ ID NO:1, deltorphin II SEQ ID NO:2 or a combination of deltorphin I SEQ ID NO:1 and II SEQ ID NO:2 may be used in the invention. Deltorphins may be obtained from frog skin extracts, or they may be purchased from a vendor such as Peninsula Laboratories, Inc. (Belmont, Calif.) or may be synthesized using a peptide synthesizer such the type available from Applied Biosystems.

Deltorphins are administered to a mammal to modulate cytokine activation by blocking one or more steps in the cytokine cascade. Deltorphins may be formulated for administration in an aqueous based liquid such as phosphate buffered saline to form an emulsion, or they may be formulated in an organic liquid such as dimethylsulfoxide to form a solution. The solution or emulsion may be administered by any route, but it is preferably administered parenterally such as by intravenous, intramuscular, intradermal or intraperitoneal injections. A preferred dose is in the range of about 0.5–20 mg, or alternatively lower doses of about 1–1000 µg of deltorphin per kg of body weight of the mammal. The time of administration of the deltorphin is preferably prior to initiation of cytokine activation. However, the deltorphin may be administered concurrently with another agent that induces cytokine activation or even subsequent to an agent that induces cytokine activation and still produce a protective effect.

Deltorphin administration should be continued on a daily basis until hepatic function returns to normal and is maintained at normal levels, preferably for at least one to two days. Hepatic injury can be determined by elevated levels of hepatic enzymes, as well as by depressed albumin levels (less than about 35 g/liter). Hepatic function is routinely monitored by quantitating serum levels of hepatic enzymes such as alanine aminotransferase (ALT) (normal<35 U/L), aspartate aminotransferase (AST) (normal<30 U/L), alkaline phosphatase (ALP) (normal≦100 U/L) and gamma glutamyltransferase (GGT) (normal≦45 U/L for males, ≦30 U/L for females), as well as bilirubin, both conjugated (normal≦0.2 mg/deciliter) and total (normal≦1.0 mg/deciliter) bilirubin. Deltorphin modulation of hepatocyte cytokine activation may be used therapeutically in a variety of hepatic injury processes. As used herein, the term hepatic injury broadly encompasses all types of injury such as hepatic trauma, physical and/or chemical insult, stress, inflammation, toxicity, disease and so on. For example, deltorphins can be used in treating hepatic injury due to alcoholic liver disease, acetaminophen toxicity, cadmium toxicity, lead poisoning, bacteremia due to, for example, Staphylococcus species, Streptococcus species, Neisseria species, Salmonella species, Shigella species, *Escherichia coli, Clostridium perfringens*, Klebsiella species, Proteus species, Enterobacter species, Bacteroides species, Brucella species, *Francisella tularensis*, Listeria monocytogenes, Acinetobacter species, *Streptobacillus moniliformis*, Vibrio species, *Helicobacter pylori*, Pseudomonas species, Haemophilus species, Bordetella pertussis, viral infections due to, for example, influenza viruses, adenoviruses, paramyxoviruses, rubella viruses, polioviruses, hepatitis viruses, herpesviruses, rabies viruses, human immunodeficiency viruses and papilloma viruses, as well as trauma, ischemia reperfusion injury and metabolic liver disease.

While the specific mechanism of deltorphin action on the modulation of cytokine mediated hepatic injury such as acute inflammatory reactions, trauma and toxin induced biological responses is unknown, deltorphins exhibit a specific and reproducible effect on decreasing hepatotoxicity. This invention will be further appreciated in light of the following example.

EXAMPLE

Hepatic failure was induced in mice by intraperitoneal injections of a mixture of lipopolysaccharide (LPS) (100 μ/kg) and D-galactosamine (GAL) (700 mg/kg) to form LPS/GAL. LPS is a bacterial endotoxin that is a major stimulus for production of many cytokines, particularly tumor necrosis factor (TNF), thought to be involved in liver injury. GAL is an amino sugar that sensitizes hepatocytes by depleting the base uridine and thus preventing hepatic transcription, and sensitizes animals to normally innocuous amounts of endotoxin or TNF. The LPS/GAL treatment induces fulminate hepatic and multiorgan failure, and serves as a model for septic shock. The major effects of LPS/GAL are elicited by the inflammatory cytokine TNF-α. Hepatocytes sensitized to TNF-α then undergo apoptosis or programmed cell death in response to inflammatory processes.

Mice were treated with deltorphin and were subsequently rendered hepatotoxic by LPS/GAL treatment. An emulsion of deltorphin I SEQ ID NO:1 (Tyr-D-Ala-Phe-Asp-Val-Val-Gly-NH$_2$) was prepared at a concentration of 80 μg/200 μl in sterile phosphate buffered saline (PBS). An emulsion of DADLE (Tyr-D-Ala-Gly-Phe-D-Leu-enkephalin) was also prepared at a concentration of 80 μg/200 μl in sterile PBS. Male BALB/c HSD mice were treated by intraperitoneal injections according to the following protocol. Control mice (n=7) received only LPS/GAL (280 μl) at 6.5 h. Deltorphin I SEQ ID NO:1 treated mice (n=15) received injections of 4 mg/kg deltorphin I SEQ ID NO:1 at 0 h, 2 h, 4 h, 6 h and 7.5 h and received an LPS/GAL injection at 6.5 h. DADLE treated mice (n 15) received 4 mg/kg DADLE at 0 h, 2 h, 4 h, 6 h and 7.5 h and received an LPS/GAL injection at 6.5 h.

Both control and treated mice were monitored at 15 h, 20 h, 40 h and 65 h after the last injection. The results are shown in the following table.

TABLE

| TREATMENT | SURVIVAL | | | |
|---|---|---|---|---|
| | 15 Hours | 20 Hours | 40 Hours | 65 Hours |
| LPS/GAL | 0 | — | — | — |
| DADLE + LPS/GAL | 3 (20%) | 3 (20%) | 3 (20%) | 3 (20%) |
| Deltorphin [SEQ ID NO:1] + LPS/GAL | 12 (80%) | 11 (73%) | 11 (73%) | 11 (73%) |

Of the seven mice receiving only LPS/GAL (control group), none survived more than 15 h post-LPS/GAL injection and some died as early as 6 to 8 h post injection. Of the 15 mice treated with DADLE, 20% (3 out of 1 5) survived for 20 h, 20% (3 out of 15) survived for 40 h and 20% (3 out of 15) survived for 65 h after the last injection. In contrast, of the 15 mice treated with deltorphin I SEQ ID NO:1, 80% (12 out of 15) survived for 15 h, 73% (11 out of 15) survived for 20 h, 73% (11 out of 15) survived for 40 h and 73% (11 out of 15) survived for 65 h after the last injection. The markedly increased survival time for deltorphin I SEQ ID NO:1 treated mice that had been made septic by LPS/GAL treatment was significant compared to mice receiving LPS/GAL only. In contrast, the survival time for DADLE treated mice was not as striking at any time point. These results indicate that treatment with deltorphin I SEQ ID NO:1 prevents acute inflammatory hepatic injury and can reduce lethality in a murine model.

A treatment for attenuating and/or preventing cytokine mediated acute inflammatory, trauma induced and toxin induced hepatic injury is thus disclosed. Deltorphins, administered at a concentration of about 0.5 mg/kg to about 20 mg/kg, or alternatively at lower concentrations of about 1–1000 μg/kg, inhibit hepatic injury and result in decreased lethality of the animal.

It should be understood that the embodiments of the present invention shown and described in the specification are only preferred embodiments of the inventors who are skilled in the art and thus are not limiting in any way. Therefore various changes, modifications or alterations to these embodiments may be made or resorted to without departing from the spirit of the invention and the scope of the following claims.

What is claimed is:

1. A method of modulating a cytokine mediated hepatic injury response in a mammal comprising administering a deltorphin selected from the group consisting of deltorphin I, deltorphin II, and combinations thereof to the mammal in a pharmaceutically acceptable formulation.

2. The method of claim 1 wherein said deltorphin is administered prior to said response.

3. The method of claim 1 wherein said deltorphin is administered subsequent to said response.

4. The method of claim 1 wherein said deltorphin is administered substantially concurrently with said response.

5. The method of claim 1 wherein said deltorphin is administered in the formulation selected from the group consisting of a solution, an emulsion and a suspension.

6. The method of claim 1 wherein said deltorphin is administered parenterally.

7. The method of claim 1 wherein said deltorphin is administered at a concentration in the range of about 0.5 mg/kg to about 20 mg/kg.

8. The method of claim 1 wherein said deltorphin is administered at a concentration in the range of about 1 µg/kg to about 1000 µg/kg.

9. A method for treating hepatic injury caused by a chemical toxin in a mammal comprising administering a pharmaceutically effective concentration of a deltorphin selected from the group consisting of deltorphin I, deltorphin II and combinations thereof.

10. The method of claim 9 wherein the chemical toxin is selected from the group consisting of ethanol, lead, cadmium, carbon tetrachloride, and acetaminophen.

11. A method for treating a bacterial or viral infection related hepatic injury in a mammal comprising administering a pharmaceutically effective concentration of a deltorphin selected from the group consisting of deltorphin I, deltorphin II, and combinations thereof.

12. The method of claim 11 wherein the bacterial or viral infection is caused by an organism selected from the group consisting of Staphylococcus species, Streptococcus species, Neisseria species, Salmonella species, Shigella species, *Escherichia coli, Clostridium perfringens*, Klebsiella species, Proteus species, Enterobacter species, Bacteroides species, Brucella species, *Francisella tularensis*, Listeria monocytogenes, Acinetobacter species, *Streptobacillus moniliformis*, Vibrio species, *Helicobacter pylori*, Pseudomonas species, Haemophilus species, Bordetella pertussis, influenza viruses, adenoviruses, paramyxoviruses, rubella viruses, polioviruses, hepatitis viruses, herpesviruses, rabies viruses, human immunodeficiency viruses and papilloma viruses.

* * * * *